United States Patent [19]

Tanaka et al.

[11] Patent Number: 4,478,961
[45] Date of Patent: Oct. 23, 1984

[54] POLYVINYL CHLORIDE COMPOSITION

[75] Inventors: Masakazu Tanaka, Osaka; Ken Murayama, Otsu, both of Japan

[73] Assignee: Toyo Boseki Kabushika Kaisha, Osaka, Japan

[21] Appl. No.: 442,705

[22] Filed: Nov. 18, 1982

[30] Foreign Application Priority Data

Nov. 18, 1981 [JP] Japan ................................ 56-185914
May 13, 1982 [JP] Japan ................................ 57-81166

[51] Int. Cl.$^3$ ........................ C08L 27/06; A61F 1/00
[52] U.S. Cl. ................................... 523/105; 525/111; 3/1.4; 604/7; 604/266; 128/DIG. 22
[58] Field of Search ................ 525/111; 524/306, 311; 3/1.4, 1.5; 523/105; 604/7

[56] References Cited

U.S. PATENT DOCUMENTS

| | | | |
|---|---|---|---|
| 2,555,062 | 5/1951 | Small et al. | 524/306 |
| 2,700,656 | 1/1955 | Emerson et al. | 524/306 |
| 3,014,882 | 12/1961 | Bruin et al. | 524/311 |
| 3,194,776 | 7/1965 | Caldwell | 524/311 |
| 3,272,769 | 9/1966 | Hunyar | 525/311 |
| 3,940,802 | 3/1976 | Sakio et al. | 523/105 |
| 4,433,012 | 2/1984 | Pusineri et al. | 523/105 |

FOREIGN PATENT DOCUMENTS 522931 10/1953 Belgium .
580036  7/1958 Canada .

Primary Examiner—Allan M. Lieberman

[57] ABSTRACT

A polyvinyl chloride composition comprising 100 parts by weight of a polyvinyl chloride and 5 to 150 parts by weight of a high molecular weight, modified polyester which is prepared by reacting (A) a polyester having a carboxyl group at terminal thereof and containing an ester unit of total carbon atoms of 8 to 10 in the diol component and the dicarboxylic acid component with (B) a compound having epoxy groups at both terminals thereof, said polyvinyl chloride composition having excellent acticoagulant activity and hence being useful for various blood handling devices including blood transmitting tube, as well as other utilities such as packages for foodstuffs as in the conventional polyvinyl chloride composition.

5 Claims, No Drawings

POLYVINYL CHLORIDE COMPOSITION

The present invention relates to an improved polyvinyl chloride composition comprising a polyvinyl chloride and a specific modified polyester as a plasticizer, and a blood transmitting tube or other blood handling devices prepared by using the polyvinyl chloride composition.

It is known that various compounds such as phthalic acid esters, aliphatic polyesters, epoxy compounds, etc. are used as a plasticizer for polyvinyl chloride. Among them, phthalic acid esters, particularly dioctyl phthalate (DOP), are widely used. These phthalic acid esters show excellent plasticizing action, but on the other hand, have some drawbacks, for example, due to substantial migration characteristics and extractability, they are easily extracted by various organic solvents, and further, when the composition is allowed to stand in contact with various other resins such as polyesters, polyamides, polyurethanes, etc., the phthalic acid esters diffuse out and migrate to the surface of the composition, thereby inducing occasionally deterioration of mechanical properties of the polyvinyl chloride composition, such as lowering of softness and elongation properties of the composition.

Besides, according to Notification No. 178 of the Ministry of Health and Welfare in Japan, the polyvinyl chloride composition used for packages for foodstuffs, etc. should show less extractability with n-hexane, etc., and hence, in view of safety of plastic packages for such utilities, the polyvinyl chloride composition used for such packages should have less extractability with organic solvents and less migration to the surface.

It is also known that a polyester produced from propylene glycol and adipic acid is used as a plasticizer for polyvinyl chloride composition instead of DOP. This polyester has a larger molecular weight than that of DOP and hence has less extractability and migration. However, it was experimentally found that the polyester shows still fairly large extractability and migration characteristics when admixed into polyvinyl chloride composition, owing to oligomers contained in the polyester.

There is also disclosed in Japanese patent publication No. 36896/1977 a low toxicity soft polyvinyl chloride composition which is prepared by admixing 100 parts by weight of a polyvinyl chloride with 40 to 110 parts by weight of a polyester urethane prepared by reacting hexamethylene diisocyanate and a polyester glycol comprising a straight aliphatic dicarboxylic acid having 6 to 12 carbon atoms and mixed diols consisting of a straight aliphatic diol having 4 to 12 carbon atoms and 4 to 12 molar % of a branched aliphatic diol having 3 to 12 carbon atoms, said diisocyanate component and polyol component being used in the ratio of 1 mole (diisocyanate) to 0.98-1.06 mole (polyol). This composition shows improved extractability and migration characteristics of the plasticizer, but owing to the remaining isocyanate groups, the composition may have toxicity against cells of human body, and further, owing to introduction of urethane bond, the polyester urethane shows lower plasticizing effect in comparison with a polyester per se.

Under the circumstances, the present inventors have intensively studied to obtain an improved plasticizer for polyvinyl chloride which has less extractability and migration characteristics, excellent plasticizing effect and less toxicity. As a result, it has been found that a specific modified polyester can give an improved soft, low toxicity polyvinyl chloride composition having no extractability and no migration without using a phthalic acid ester as a plasticizer.

An object of the present invention is to provide an improved polyvinyl chloride composition having low toxicity and no extractability and migration characteristics wherein a specific modified polyester is used as a plasticizer. Another object of the invention is to provide a polyvinyl chloride composition which is useful as packages for foodstuffs, medical devices, particularly as blood transmitting tube and blood handling devices. A further object of the invention is to provide a blood transmitting tube and blood handling device prepared by using the improved polyvinyl chloride composition as set forth above. These and other objects and advantages of the invention will be apparent from the following description.

The improved polyvinyl chloride composition of the present invention comprises 100 parts by weight of a polyvinyl chloride and 5 to 150 parts by weight of a high molecular weight, modified polyester which is prepared by reacting a polyester having a carboxyl group at either one or both terminals thereof and containing an ester unit of total carbon atoms of 8 to 20 in the diol component and dicarboxylic acid component with a compound having epoxy groups at both terminals thereof.

The above high molecular weight, modified polyester is useful as a plasticizer and can give a polyvinyl chloride composition having improved extractability, migration characteristics and toxicity as well as excellent mechanical properties such as excellent softness, elongation, low-temperature flexing property, wear resistance, etc. The polyvinyl chloride composition of the present invention is also excellent in anticoagulant activity.

The high molecular weight, modified polyester is prepared by reacting (A) a polyester having a carboxyl group at either one or both terminals and containing an ester unit of total carbon atoms of 8 to 20 in the diol component and the dicarboxylic acid component with (B) a compound having epoxy groups at both terminals thereof.

The diol component of the polyester having a carboxyl group at either one or both terminals (A) includes aliphatic and/or alicyclic diols such as ethylene glycol, propylene glycol, tetramethylene glycol, hexamethylene glycol, neopentyl glycol, heptamethylene glycol, octamethylene glycol, nonamethylene glycol, decamethylene glycol, cyclohexanediol, cyclohexanedimethanol. The dicarboxylic acid component includes glutaric acid, adipic acid, pimelic acid, cork acid, azelaic acid, sebacic acid, undecadionic acid, dodecadionic acid.

The ester unit consisting of the diol component and the dicarboxylic acid component has total carbon atoms of 8 to 20, preferably 10 to 15. The diols and dicarboxylic acids should be elected so as to satisfy the above range of total carbon atom in the ester unit. When the total carbon atom in the ester unit is less than 8, the modified polyester shows inferior compatibility with polyvinyl chloride, and hence can not give a uniform composition, and further, when the total carbon atom is over 20, the modified polyester shows also inferior compatibility.

The polyester (A) is prepared by a conventional method and apparatus, for example, by reacting with stirring the starting diol and dicarboxylic acid at a temperature of 150° to 260° C. in an esterification apparatus. In this reaction, there may be used an appropriate esterification catalyst, such as phosphoric acid, phosphorous acid, sulfuric acid, p-toluenesulfonic acid, methane sulfonic acid, stannous oxalate, alkyl lead oxide, tetrabutyl titanate, zinc acetate, sodium carbonate, which is used in an amount of 0.01 to 0.5 % by weight. The reaction is preferably carried out by heating the mixture at 150° to 260° C. under atmospheric pressure for 2 to 5 hours, and then reducing gradually the pressure to 0.1 to 50 mmHg, by which the remaining water is completely removed.

The polyester (A) thus obtained is usually in a mixture of polyesters having a carboxyl group at either one terminal and polyesters having carboxyl groups at both terminals and has a number average molecular weight of 500 to 20,000, preferably 1,000 to 8,000 and an acid value of 3 to 225, preferably 7 to 110.

The compound having epoxy groups at both terminals (B) includes compounds of the following fromulae (I), (II) and (III):

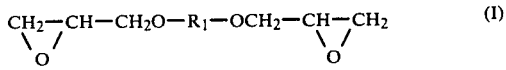

wherein $R_1$ is an alkylene having 2 to 50 carbon atoms, an aralkylene having 7 to 50 carbon atoms, an oxyalkylene having 2 to 50 carbon atoms, a group of the formula:

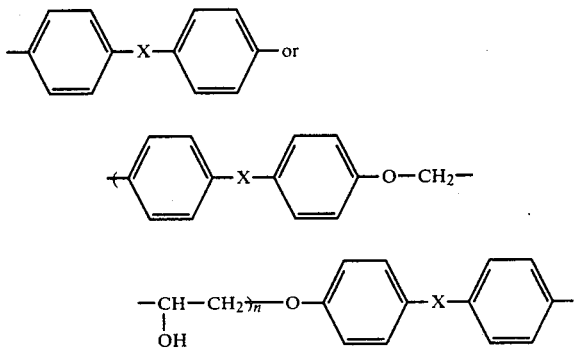

wherein X is isopropylidene, methylene, sulfonyl or oxy, and n is an integer of 1 to 10,

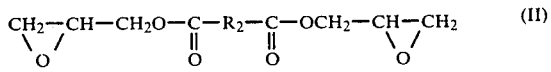

wherein $R_2$ is an alkylene having 2 to 50 carbon atoms, an alkenylene having 2 to 50 carbon atoms, an aralkylene having 7 to 50 carbon atoms, or an aromatic group having 6 to 30 carbon atoms,

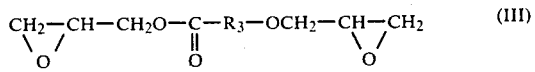

wherein $R_3$ is an alkylene having 2 to 50 carbon atoms, a hydroxyalkylene having 2 to 50 carbon atoms, an aralkylene having 7 to 50 carbon atoms, or an aromatic group having 6 to 30 carbon atoms.

The compound having epoxy groups of the formula (I) includes compounds prepared by diglycidyl etherification of hydroxy groups at both terminals of a compound selected from aliphatic diols having 2 to 50 carbon atoms (e.g. tetramethylene glycol, pentamethylene glycol, hexamethylene glycol), aromatic diols having 6 to 30 carbon atoms (e.g. 4,4'-isopropylidenediphenol, 4,4'-dihydroxyphenylmethane, 4,4'-dihydroxyphenylsulfone), and polyalkylene glycols (e.g. polyethylene glycol having a molecular weight of 100 to 1,000, polypropylene glycol, polytetramethylene glycol, a copolymer of ethylene oxide and propylene oxide), and further includes epoxy resins having epoxy groups at both terminals and having a molecular weight of 400 to 2,000 which are obtained from 4,4'-isopropylidenediphenol and epichlorohydrin.

The compound having epoxy groups of the formula (II) includes compounds prepared by diglycidyl esterification of carboxyl groups at both terminals of a compound selected from aliphatic saturated dicarboxylic acids having 2 to 50 carbon atoms (e.g. adipic acid, azelaic acid, sebacic acid, dimer acids), aliphatic unsaturated dicarboxylic acids having 4 to 50 carbon atoms (e.g. maleic acid, fumaric acid), aromatic dicarboxylic acids having 8 to 30 carbon atoms (e.g terephthalic acid, isophthalic acid), aliphatic dicarboxylic acids containing an aromatic group on the side chain (e.g. 1,2-bis(ω-hydroxycarbonylhexamethylphenyl)ethane).

The compound having epoxy groups of the formula (III) includes glycidyl ether glycidyl ester of hydroxycarboxylic acids such as ε-capronic acid, benzoic acid, or the like.

The high molecular weight, modified polyester of the present invention can be prepared by reacting 1 mole of the above polyester having a carboxyl group at either one or both terminals (A) and 0.5 to 1.5 mole, preferably 0.7 to 1.2 mole, of the above compound having epoxy groups at both terminals (B) under the conditions of a temperature of 100° to 250° C., preferably 120° to 230° C., under nitrogen gas stream, with stirring for 0.1 to 10 hours. In this reaction, there may be used a catalyst which is usually used for ring-opening reaction of epoxy group, preferably an alkali metal salt of an aliphatic mono- or di-carboxylic acid having 6 to 50 carbon atoms. The catalyst is usually used in an amount of 0.05 to 0.5 % by weight. The high molecular weight, modified polyester thus obtained has a reduced viscosity of 0.30 or more, preferably 0.50 or more, which is measured in a concentration of 0.4 g/dl in chloroform at 30° C. The molecular weight of the modified polyester is in the range of 1,000 to 100,000, preferably 3,000 to 50,000.

In the preparation of the polyvinyl chloride composition, the high molecular, modified polyester is mixed with a polyvinyl chloride in an amount of 5 to 150 parts by weight per 100 parts by weight of the polyvinyl chloride. In order to obtain a soft polyvinyl chloride composition, the polyester is preferably used in an amount of 40 parts by weight or more. When the polyester is used in an amount of over 150 parts by weight, the resulting composition shows highly increased tackiness which causes difficulty in handling thereof, and on the other hand, when the amount of polyester is less than 5 parts by weight, the desired plasticizing action is not achieved. The modified polyester is mixed with the polyvinyl chloride by a conventional method using a conventional mixing machine such as roll mixer, Henschel mixer, Banbury mixer, or the like. In the mixing, there may optionally be used an appropriate solvent such as tetrahydrofuran, chloroform, tetrachloroethane, or the like.

In processing of polyvinyl chloride composition, some additives such as stabilizers and lubricating agents are usually incorporated. The polyvinyl chloride composition of the present invention is also incorporated with these conventional additives. The stabilizers and lubricating agents include all conventional agents, but a combination of an epoxy stabilizer, calcium stearate and zinc stearate is particularly preferable in order to use the composition for packages for foodstuffs and medical devices.

The polyvinyl chloride composition of the present invention has sufficient softness even though no phthalic plasticizer such as DOP, is used, and hence, has no problem such as extraction, migration and toxicity due to a low molecular weight plasticizer and has excellent mechanical properties such as excellent softness, elongation, low-temperature flexing, wear resistance, as well as good operability.

The polyvinyl chloride composition of the present invention has also excellent anticoagulant activity, and hence, can be widely used for the preparation of various medical devices and materials such as blood circuit vessel, syringe, blood bag, catheter, cannula, shunt, or the like, and further materials which are used in direct contact with blood, such as artificial lung, artificial heart, artificial kidney, or a part thereof. Accordingly, the present invention provides also a blood transmitting tube and blood handling devices prepared by using the polyvinyl chloride composition. That is, the polyvinyl chloride composition can be processed to form blood transmitting tube and blood handling devices having various shapes by kneading with a conventional kneading machine, pelletizing and then extruding with a conventional extruder. Alternatively, the blood transmitting tube and blood handling devices may be prepared by coating conventional tube and devices with the polyvinyl chloride composition of the present invention. The tube and devices may also be prepared by mixing well the high molecular weight, modified polyester and polyvinyl chloride in liquid state and optionally other conventional additives such as a stabilizer and lubricating agent, and then forming into the derised tube and devices or coating the mixture onto conventional tube and devices.

The polyvinyl chloride composition of the present invention is also useful for various utilities, for which the conventional polyvinyl chloride composition has been used, for example, packages for foodstuffs, hoses and belts for foodstuffs, artificial leathers, toys, or the like.

The present invention is illustrated by the following Preparations, Examples and Reference Examples, but is not construed to be limited thereto. In these Preparations and Examples, "part" is part by weight, and the viscosity ($\eta sp/c$) was measured in a solution in chloroform in a concentration of the polymer of 0.4 g/dl, at 30° C.

Besides, the acid value and hydroxy value of the polyester were measured in the following manner:

(a) Acid value:

The polymer to be measured (1 g) was precisely weighed and dissolved in a mixture of methyl cellosolvedioxane (1:1 by volume) (50 ml). The solution was titrated with 1/10 N KOH having a predetermined factor by a potentiometric titration apparatus (Comtite-7, manufactured by Hiranuma Sangyo K.K.), and the final point (maximum point of potential variation) was measured. As a control, the same procedure was repeated by using merely a mixture of methyl cellosolve-dioxane instead of solution. The acid value (mg KOH/g) was calculated by the following equation.

$$\text{Acid value} = \frac{(A - B) \times F \times 5.61}{S}$$

wherein A is ml of 1/10 N KOH required for titration of the sample solution, B is ml of 1/10 N KOH required for titration of the control mixture, F is the factor of 1/10 N KOH, and S is weight (g) of the sample (i.e. polymer).

(b) Hydroxy value:

The polymer to be measured (about 5 g) was taken in a 100 ml flask and the weight of the polymer was precisely measured. To the flask was added an acetylating reagent (pyridine:acetic anhydride = 15:1 by volume, 10 ml) to dissolve the polymer. After reacting the mixture at 100° C. for 60 minutes, the reaction mixture was cooled and thereto was added water (5 ml), and then, the mixture was allowed to stand for 10 minutes. The reaction mixture was titrated with $\frac{1}{2}$ N KOH having a predetermined factor by using phenolphthalein as an indicator. As a control, the above procedure was repeated without using the polymer. The hydroxy value (mg KOH/g) was calculated by the following equation.

$$\text{Hydroxy value} = AV + \frac{(B - A) \times 0.5 \times F \times 56.11}{S}$$

wherein A is ml of $\frac{1}{2}$ N KOH required for the titration of the sample solution, B is ml of $\frac{1}{2}$ N KOH required for the titration of the control, F is the factor of $\frac{1}{2}$ N KOH, S is the weight of the sample (i.e. polymer), and AV is the acid value (mg KOH/g).

PREPARATION 1

Adipic acid (1524 parts), 1,6-hexanediol (1182 parts), tetrabutyl titanate (0.108 part) and trimethyl phosphate (0.089 part) are charged into an autoclave and are reacted with stirring under nitrogen gas stream while raising the temperature to 150° to 230° C. over a period of 2 hours with removing the produced water. With keeping the temperature at 230° C., the pressure in autoclave is gradually reduced till 0.1 mmHg over a period of 60 minutes, and then the mixture is further reacted at 230° C. under reduced pressure of 0.1 mmHg for 60 minutes to give a polyester having a carboxyl group at terminal thereof and having an acid value of 24.7 and a hydroxy value of 0.50.

The polyester thus obtained (1500 parts), an epoxy resin YD-128 (manufactured by Toto Kasei K.K., epoxy equivalent: 192.3 g/equivalent, 88.9 parts) and disodium salt of Dimer acid (disodium salt of Versadyme ®️ 288, manufactured by Henkel Japan; 3.0 parts) are charged into an autoclave, and the mixture is reacted with stirring under nitrogen gas at 180° C. for 4 hours to give a modified polyester ($\eta sp/c = 0.756$) (hereinafter, referred to as "Modified Polyester A").

PREPARATION 2

Adipic acid (1524 parts), 1,6-hexanediol (1061 parts), neopentyl glycol (104 parts), tetrabutyl titanate (0.108 part) and trimethyl phosphate (0.089 part) are charged into an autoclave, and the mixture is reacted in the same manner as described in Preparation 1 to give a polyester having a carboxyl group at terminal thereof and having an acid value of 27.0 and a hydroxy value of 0.51.

The polyester thus obtained (1500 parts), an epoxy resin YD-128 (88.9 parts) and disodium salt of Dimer acid (3.0 parts) are charged into an autoclave, and the mixture is reacted in the same manner as described in Preparation 1 to give a modified polyester ($\eta sp/c = 0.80$) (hereinafter, referred to as "Modified Polyester B").

PREPARATION 3

Adipic acid (1524 parts), 1,4-butanediol (899 parts), tetrabutyl titanate (0.108 part) and trimethyl phosphate (0.089 part) are charged into an autoclave, and the mixture is reacted in the same manner as described in Preparation 1 to give a polyester having a carboxyl group at terminal thereof and having an acid value of 38.7 and a hydroxy value of 0.48.

The polyester thus obtained (1500 parts), diglycidyl sebacate (153 parts) and disodium salt of Dimer acid (3.0 parts) are charged into an autoclave, and the mixture is reacted in the same manner as described in Preparation 1 to give a modified polyester ($\eta sp/c = 0.78$) (hereinafter, referred to as "Modified Polyester C").

PREPARATION 4

Sebacic acid (1524 parts), 1,6-hexanediol (762 parts), neopentyl glycol (75 parts), tetrabutyl titanate (0.108 part) and trimethyl phosphate (0.089 part) are charged into an autoclave and the mixture is reacted in the same manner as described in Preparation 1 to give a polyester having a carboxyl group at terminal thereof and having an acid value of 26.8 and a hydroxy value of 0.32.

The polyester thus obtained (1500 parts), diglycidyl sebacate (87 parts) and disodium salt of Dimer acid (3.0 parts) are charged into an autoclave and the mixture is reacted in the same manner as described in Preparation 1 to give a modified polyester ($\eta sp/c = =0.83$) (hereinafter, referred to as "Modified Polyester D").

PREPARATION 5

Sebacic acid (1524 parts), ethylene glycol (460 parts), tetrabutyl titanate (0.108 part) and trimethyl phosphate (0.089 part) are charged into an autoclave and the mixture is reacted in the same manner as described in Preparation 1 to give a polyester having a carboxyl group at terminal thereof and having an acid value of 26.5 and a hydroxy value of 0.35.

The polyester thus obtained (1500 parts), an epoxy resin YD-128 (88.9 parts) and disodium salt of Dimer acid (3.0 parts) are charged into an autoclave and the mixture is reacted in the same manner as described in Preparation 1 to give a modified polyester ($\eta sp/c = 0.77$) (hereinafter, referred to as "Modified Polyester E").

PREPARATION 6

Adipic acid (3629 parts) and 1,6-hexanediol (3545 parts) are charged into an autoclave, and the mixture is reacted with stirring under nitrogen gas stream while raising the temperature to 150 to 230° C. over a period of 2 hours with removing the produced water. Tetrabutyl titanate (0.36 part) is added to the reaction mixture, and with keeping the temperature at 230° C., the pressure of autoclave is gradually reduced till 0.1 mmHg over a period of 60 minutes. The mixture is further reacted at 230° C. under reduced pressure of 0.1 mmHg for 3 hours to give a polyester ($\eta sp/c = 0.33$) (hereinafter, referred to as "Polyester F").

PREPARATION 7

A polyester glycol (molecular weight: 2,000) is prepared from mixed diol consisting of 1,6-hexanediol and neopentyl glycol (9:1 by mole) and adipic acid. This polyester glycol (1 mole) and hexamethylene diisocyanate (1.03 mole) are charged into an autoclave and the mixture is reacted with stirring under nitrogen gas stream at 160° C. for 2 hours to give a polyuethane ($\eta sp/c = 0.88$) (hereinafter, referred to as "Polyurethane G").

PREPARATION 8

Dimer acid ($HOOC_{34}H_{68}COOH$) (5898 parts), 1,6-hexanediol (1182 parts), tetrabutyl titanate (0.35 part) and trimethyl phosphate (0.30 part) are charged into an autoclave and the mixture is reacted in the same manner as described in Preparation 1 to give a polyester having a carboxyl group at terminal thereof and having an acid value of 20.3 and a hydroxy value of 0.22.

The polyester thus obtained (1500 parts), epoxy resin YD-128 (58.4 parts) and disodium salt of Dimer acid ($NaOOCC_{34}H_{68}COONa$) (3.0 g) are charged into an autoclave and the mixture is reacted in the same manner as described in Preparation 1 to give a modified polyester ($\eta sp/c = 0.78$) (hereinafter, referred to as "Modified Polyester H").

PREPARATION 9

Adipic acid (1452 parts), 1,6-hexanediol (788 parts), tetrabutyl titanate (0.108 part) and trimethyl phosphate (0.089 part) are charged into an autoclave, and the mixture is reacted in the same manner as described in Preparation 1 to give a polyester having a carboxyl group at terminal thereof and having an acid value of 251 and a hydroxy value of 0.15.

The polyester thus obtained (1500 parts), epoxy resin YD-127 (1032 parts) and disodium salt of Dimer acid (3.0 parts) are charged in an autoclave, and the mixture is reacted in the same manner as described in Preparation 1 to give a modified polyester ($\eta sp/c = 0.538$) (hereinafter, referred to as "Modified Polyester I").

PREPARATION 10

Adipic acid (1452 parts), 1,6-hexanediol (1182 parts), tetrabutyl titanate (0.108 part) and trimethyl phosphate (0.089 part) are charged into an autoclave and are reacted with stirring under nitrogen gas stream while raising the temperature to 150 to 230° C. over a period of 2 hours with removing the produced water. With keeping the temperature at 230° C., the pressure in autoclave is gradually reduced till 0.1 mmHg over a period of 60 minutes and the temperature is further raised to 250° C., and then, the mixture is further reacted at 250° C. under reduced pressure of 0.1 mmHg for 3 hours to give a polyester having carboxyl group at terminal thereof and having an acid value of 2.7 and a hydroxy value of 1.8.

The polyester thus obtained (1500 parts), epoxy resin YD-128 (13.5 parts) and disodium dimerate (1.0 part) are charged into an autoclave and reacted with stirring under nitrogen gas stream at 180° C. for 8 hours to give a modified polyester ($\eta sp/c\ sp/c = 0.956$) (hereinafter, referred to as "Modified Polyester J").

EXAMPLES 1 TO 5 AND REFERENCE EXAMPLES 1 TO 6

Components as shown in Table 1 are used.

TABLE 1

| Components | Example 1 | Example 2 | Example 3 | Example 4 | Example 5 | Ref. 1 | Ref. 2 | Ref. 3 | Ref. 4 | Ref. 5 | Ref. 6 |
|---|---|---|---|---|---|---|---|---|---|---|---|
| Modified Polyester A | 80 | | | | | | | | | | |
| Modified Polyester B | | 80 | | | | | | | | | |
| Modified Polyester C | | | 80 | | | | | | | | |
| Modified Polyester D | | | | 80 | | | | | | | |
| Modified Polyester E | | | | | 80 | | | | | | |
| Polyester F | | | | | | 80 | | | | | |
| Polyurethane G | | | | | | | 80 | | | | |
| Modified polyester H | | | | | | | | 80 | | | |
| Modified polyester I | | | | | | | | | 80 | | |
| Modified polyester J | | | | | | | | | | | 80 |
| Polyvinyl chloride (polymerization degree: 1100) | 100 | 100 | 100 | 100 | 100 | 100 | 100 | 100 | 100 | 100 | 100 |
| DOP | | | | | | | 60 | | | | |
| Epoxy stabilizer | 5 | 5 | 5 | 5 | 5 | 5 | 5 | 5 | 5 | 5 | 5 |
| Calcium stearate | 0.5 | 0.5 | 0.5 | 0.5 | 0.5 | 0.5 | 0.5 | 0.5 | 0.5 | 0.5 | 0.5 |
| Zinc stearate | 1 | 1 | 1 | 1 | 1 | 1 | 1 | 1 | 1 | 1 | 1 |

The components are mixed and kneaded for 10 minutes with a vapor heating type 8 inch mixing roll (roll temperature: 150–160° C.) to prepare a polyvinyl chloride composition. The polyvinyl chloride composition is drawn from the mixing roll in the shape of a sheet to give a sheet (thickness: 2 mm). The above procedure is carried out under the conditions of pressing temperature: 160–170° C., pressing time: 3 minutes, pressing pressure: 100–120 kg/cm2, cooling time: 5 minutes, and pressure at cooling: 130–150 kg/cm2

Various physical properties of the above product were tested in the following manner:

(1) 100% modulus (degree of plastication) . . . It was measured in the method as defined in Japanese Industrial Standard (JIS) K 6301.

(2) Low-temperature flexing fatigue . . . A test piece (sheet of thickness: 2 mm, width: 2.5 cm and length: 15 cm, at the central area thereof being cut in a width of 2 mm in the direction of width) was tested with Demattia Flex Cracking flexing fatigue tester at a temperature of −10±1° C., and the number of flexing was counted until the sheet was broken.

(3) Extractability . . . It was measured by the method as defined in Notification No. 178 of the Ministry of Health and Welfare in Japan.

The test results are shown in Table 2.

As is clear from the above test results, the polyvinyl chloride compositions of the present invention are excellent in softness, low-temperature characteristics and extractability.

Anticoagulant activity of the polyvinyl chloride compositions obtained in the above Examples 1 to 5 and Reference Examples 1 to 6 was measured in the following manner:

The anticoagulant acitvity was measured by a column method developed by Sakurai et al [cf. Makromol. Chem., 179, 1121 (1978)].

TABLE 2

| | 100% Modulus (kg/cm$^2$) | Low-temperature flexing fatigue (number of flexing) | Extractability |
|---|---|---|---|
| Example 1 | 49 | More than 8000 | Not extractable |
| Example 2 | 45 | " | " |
| Example 3 | 51 | " | " |
| Example 4 | 48 | " | " |
| Example 5 | 48 | " | " |
| Ref. Ex. 1 | 53 | Less than 7300 | Extractable |
| Ref. Ex. 2 | 54 | Less than 6800 | Not extractable |
| Ref. Ex. 3 | 58 | Less than 5000 | Extractable |
| Ref. Ex. 4 | 63 | Less than 4000 | Not extractable |
| Ref. Ex. 5 | 65 | Less than 4000 | Extractable |
| Ref. Ex. 6 | 54 | Less than 7000 | " |

That is, glass beads (diameter: 200μ) were coated with a 0.5 % solution of the polyvinyl chloride composition in tetrahydrofuran, which were dried at 40° C. under atmospheric pressure for 12 hours and further dried at 40° C. under reduced pressure. The coated glass beads (1.0 g) were thickly packed in a commercial available medical tube having cocks at both ends (inside diameter: 3.0 mm) in length of 10 cm. The tube was fulled with physiological saline solution.

Fresh blood (2 ml) was collected from jugular vein of an adult dog with a 10 ml volume disposable syringe for medical use. The collected blood was immediately set in a syringe pump which could push out the content at a fixed flow rate. The beads-packed column prepared above was connected to the syringe at the tip thereof (after removal of needle). The blood was flowed through the column at a flow rate of 1.0 mg/minute for 1 minute. The blood passed through the column was collected into a commercially available EDTA-treated plastic bottle, and the blood platelet in the passed blood was counted by Brecher Cronkite method. Number of blood platelet adhered to the beads was calculated by deducting the number of blood platelet in the blood passed through the column from the number of blood platelet in the blood before passing the column. As a control, glass beads coated with polyvinyl chloride were used instead of those coated with polyvinyl chloride composition.

Relative adhesion value (i.e. comparison of blood platelet adhesion between the material to be tested and that of control) was calculated by the following equation. When this value is smaller, it means that the adhesion of blood platelet is less, i.e. the material shows superior anticoagulant activity.

$$\text{Relative adhesion value} = \frac{\text{Number of blood platelet adhered to beads coated with polyvinyl chloride composition}}{\text{Number of blood platelet adhered to beads coated with polyvinyl chloride}}$$

The test results are shown in Table 3.

TABLE 3

| Example No. | Relative adhesion value (value in polyvinyl chloride = 1.00) |
|---|---|
| Example 1 | 0.62 |
| Example 2 | 0.60 |
| Example 3 | 0.61 |
| Example 4 | 0.64 |
| Example 5 | 0.59 |
| Ref. Ex. 1 | 1.10 |
| Ref. Ex. 2 | 0.97 |
| Ref. Ex. 3 | 1.40 |
| Ref. Ex. 4 | 1.45 |
| Ref. Ex. 5 | 1.15 |
| Ref. Ex. 6 | 1.10 |

As is clear from the above test results, the polyvinyl chloride compositions of the present invention showed significantly improved blood compatibility.

EXAMPLES 6 AND 7 AND REFERENCE EXAMPLE 7

By using the components as shown in Table 4, polyvinyl chloride compositions and further sheets were prepared in the same manner as described in Examples 1 to 5.

TABLE 4

| | Amount (part by weight) | | |
|---|---|---|---|
| | Example | | Reference |
| Components | 6 | 7 | Example 7 |
| Modified Polyester A | 70 | | |
| Modified Polyester B | | 70 | |
| Polyvinyl chloride (polymerization degree = 1100) | 100 | 100 | 100 |
| DOP | | | 60 |
| Epoxy stabilizer | 5 | 5 | 5 |
| Calcium stearate | 0.5 | 0.5 | 0.5 |
| Zinc stearate | 1 | 1 | 1 |

As to the sheets thus obtained, the extractability and anticoagulant activity were tested in the same manner as described above. The results are shown in Table 5.

TABLE 5

| Example No. | Extractability | Relative adhesion value |
|---|---|---|
| Example 6 | Not extractable | 0.67 |
| Example 7 | " | 0.66 |
| Ref. Ex. 7 | Extractable | 1.54 |

EXAMPLE 8

The polyvinyl composition obtained in Example 6 is extruded with a conventional extruder to form a tube (inside diameter: 5 mm).

The tube was used as a blood circuit for an artificial kidney and tested by using an adult dog. As a result, it could be used for a long period of time without any disorders such as coagulation of blood or variation of concentration of blood.

EXAMPLE 9

The polyvinyl chloride composition obtained in Example 6 is formed into a catheter (outer diameter: 2 mm) by a conventional melt processing.

When this catheter was used instead of a commercially available catheter made of polyvinyl chloride, it could be used without any problem of thrombus.

EXAMPLE 10

Modified Polyester A prepared in Preparation 1 (40 parts) and polyvinyl chloride (polymerization degree: 1100) (60 parts) are dissolved in tetrahydrofuran (900 parts) to give a polyvinyl chloride composition.

The polyvinyl chloride composition was coated onto the inner surface of a commercially available polyurethane tube (inside diameter: 1.5 mm, outer diameter: 2.5 mm). The tube was used as an A-V shunt in femoral artery and vein of Japanese white rabbit. As a result, it could continuously be used for 13 days (in average in 5 rabbits), which means that the tube of the present invention is excellent as a blood transmitting tube.

What is claimed is:

1. A polyvinyl chloride composition, which comprises 100 parts by weight of polyvinyl chloride and 5 to 150 parts by weight of a modified polyester having a number average molecular weight of 1,000 to 100,000 which is prepared from (A) a polyester having a carboxyl group at terminal thereof and containing an ester unit of total carbon atoms of 8 to 20 in the diol component and the dicarboxylic acid component, said polyester (A) having a number average molecular weight of 500 to 20,000 and having an acid value of 3 to 225, and (B) a compound having epoxy groups at both terminals thereof using an alkali metal salt of an aliphatic mono- or di-carboxylic acid having 6 to 50 carbon atoms as a catalyst.

2. A polyvinyl chloride composition according to claim 1, wherein the polyester having a carboxyl group at terminal thereof (A) has an ester unit of total carbon atoms of 10 to 15.

3. A polyvinyl chloride composition according to claim 1, wherein the compound having epoxy groups at both terminals thereof (B) is a compound selected from the group consisting of compounds of the formulae:

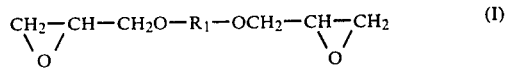

wherein $R_1$ is an alkylene having 2 to 50 carbon atoms, an aralkylene having 7 to 50 carbon atoms, an oxyalkylene having 2 to 50 carbon atoms, a group of the formula:

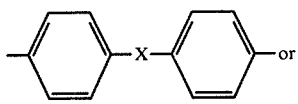

or

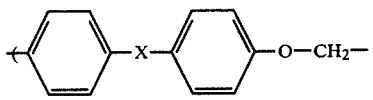

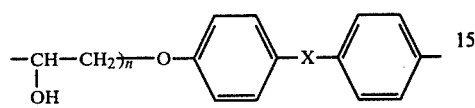

wherein X is isopropylidene, methylene, sulfonyl or oxy, and n is an integer of 1 to 10,

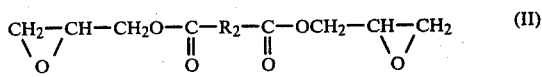 (II)

wherein R2 is an alkylene having 2 to 50 carbon atoms, an alkenylene having 2 to 50 carbon atoms, an aralkylene having 7 to 50 carbon atoms, or an aromatic group having 6 to 30 carbon atoms, and

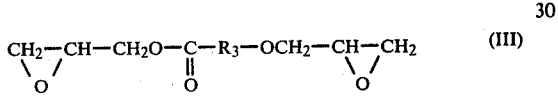 (III)

wherein R3 is an alkylene having 2 to 50 carbon atoms, a hydroxyalkylene having 2 to 50 carbon atoms, an aralkylene having 7 to 50 carbon atoms, or an aromatic group having 6 to 30 carbon atoms.

4. Blood transmitting tube and blood handling device, which comprises the polyvinyl chloride composition as set forth in claim 1 or a conventional tube or device coated with the polyvinyl chloride composition.

5. A blood transmitting tube or blood handling device, which is produced by processing a polyvinyl chloride composition to form the desired tube or device, or by coating the polyvinyl chloride composition onto a conventional tube or device, said polyvinyl chloride composition comprising 100 parts by weight of a polyvinyl chloride and 5 to 150 parts by weight of a modified polyester having a number average molecular weight of 1,000 to 100,000 which is prepared from (A) a polyester having a carboxyl group at terminal thereof and containing an ester unit of total carbon atoms of 8 to 20 in the diol component and the dicarboxylic acid component, said polyester having a number average molecular weight of 500 to 20,000 and having an acid value of 3 to 225, and (B) a compound having epoxy groups at both terminals thereof selected from the group consisting of compounds of the formula:

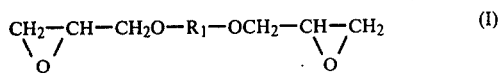 (I)

wherein R1 is an alkylene having 2 to 50 carbon atoms, an aralkylene having 7 to 50 carbon atoms, an oxyalkylene having 2 to 50 carbon atoms, a group of the formula:

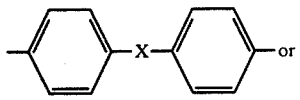

or

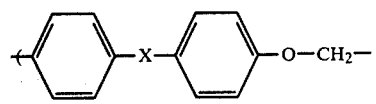

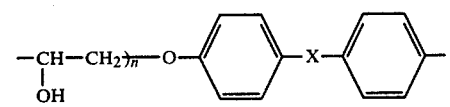

wherein X is isopropylidene, methylene, sulfonyl or oxy, and n is an integer of 1 to 10,

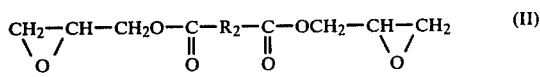 (II)

wherein R2 is an alkylene having 2 to 50 carbon atoms, an alkylene having 2 to 50 carbon atoms, an aralkylene having 7 to 50 carbon atoms, or an aromatic group having 6 to 30 carbon atoms, and

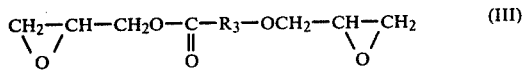 (III)

wherein R3 is an alkylene having 2 to 50 carbon atoms, a hydroxyalkylene having 2 to 50 carbon atoms, an aralkylene having 7 to 50 carbon atoms, or an aromatic group having 6 to 30 carbon atoms, using an alkali metal salt of an aliphatic mono- or di-carboxylic acid having 6 to 50 carbon atoms as a catalyst.

* * * * *

UNITED STATES PATENT AND TRADEMARK OFFICE
CERTIFICATE OF CORRECTION

PATENT NO. : 4,478,961
DATED : October 23, 1984
INVENTOR(S) : MASAKAZU TANAKA and KEN MURAYAMA It is certified that error appears in the above-identified patent and that said Letters Patent is hereby corrected as shown below:

Column 13, line 26, "R2" should be --$R_2$--.
Column 13, line 35, "R3" should be --$R_3$--.
Column 14, line 39, "R2" should be --$R_2$--.
Column 14, line 40, "alkylene" should be --alkenylene--.
Column 14, line 48, "R3" should be --$R_3$--.

Signed and Sealed this

Thirtieth Day of April 1985

[SEAL]

Attest:

DONALD J. QUIGG

Attesting Officer

Acting Commissioner of Patents and Trademarks